(12) United States Patent
Branch

(10) Patent No.: US 8,436,509 B1
(45) Date of Patent: May 7, 2013

(54) HIGH-FREQUENCY SHEAR-HORIZONTAL SURFACE ACOUSTIC WAVE SENSOR

(75) Inventor: Darren W. Branch, Albuquerque, NM (US)

(73) Assignee: Saudia Corporation, Albuquerque, NM (US)

(*) Notice: Subject to any disclaimer, the term of this patent is extended or adjusted under 35 U.S.C. 154(b) by 419 days.

(21) Appl. No.: 12/169,239

(22) Filed: Jul. 8, 2008

(51) Int. Cl.
*H03H 9/125* (2006.01)

(52) U.S. Cl.
USPC ............... 310/313 R; 310/313 D; 310/313 B

(58) Field of Classification Search .............. 310/313 D, 310/313 R, 313 B
See application file for complete search history.

(56) References Cited

U.S. PATENT DOCUMENTS

| | | | | |
|---|---|---|---|---|
| 3,736,044 | A * | 5/1973 | Lean et al. | 359/305 |
| 4,162,465 | A | 7/1979 | Hunsinger et al. | |
| 5,073,763 | A * | 12/1991 | Wright | 333/193 |
| 6,373,353 | B1 * | 4/2002 | Takeuchi et al. | 333/193 |
| 6,429,569 | B1 * | 8/2002 | Kadota | 310/313 R |
| 6,777,855 | B2 | 8/2004 | Bergmann et al. | |
| 6,870,302 | B2 * | 3/2005 | Nakamura et al. | 310/313 B |
| 7,027,921 | B2 * | 4/2006 | Kalantar-Zadeh et al. | 702/2 |
| 7,173,360 | B2 | 2/2007 | Hartmann et al. | |
| 2002/0057035 | A1 * | 5/2002 | Nakamura et al. | 310/313 B |
| 2002/0158715 | A1 * | 10/2002 | Nakamura et al. | 333/193 |
| 2005/0088057 | A1 * | 4/2005 | Kando | 310/313 B |
| 2006/0145568 | A1 * | 7/2006 | Morita et al. | 310/313 A |
| 2007/0068256 | A1 * | 3/2007 | Xu et al. | 73/597 |
| 2007/0159027 | A1 * | 7/2007 | Tsai et al. | 310/313 R |

OTHER PUBLICATIONS

Qiao, D. et al, "General Green's Functions for SAW Device Analysis", IEEE Transactions on Ultrasonics, Ferroelectrics, and Frequency Control, vol. 46, No. 5, Sep. 1999, pp. 1242-1253.
Berkenpas, E. et al, "LGS Shear Holizontal SAW Devices for Biosensor Applications", 2003 IEEE Ultrasonics Symposium, pp. 1404-1407.
Darren W. Branch et al, "Low-level detection of a *Bacillus anthracis* stimulant using Love-wave biosensors on 36° YX LiTaO₃", Biosensors and Bioelectronics, vol. 19, (2004) 849-859.
Z. Wang et al, "Sensitivity analysis for Love mode acoustic gravimetric sensors", Applied Physics Letters, 1994, vol. 64, No. 22, pp. 2940-2942.
M. Pereira da Cunha et al, "High Coupling, Zero TCD SH Wave on LGX", 2003 IEEE Ultrasonics Symposium, pp. 381-384.
Electra Gizeli et al, "A Novel Love-Plate Acoustic Sensor Utilizing Polymer Overlayers", IEEE Transactions on Ultrasonics, Ferroelectrics, and Frequency Control, vol. 39, No. 5, Sep. 1992, pp. 657-659.

(Continued)

*Primary Examiner* — Thomas Dougherty
*Assistant Examiner* — Bryan Gordon
(74) *Attorney, Agent, or Firm* — Kevin W. Bieg

(57) ABSTRACT

A Love wave sensor uses a single-phase unidirectional interdigital transducer (IDT) on a piezoelectric substrate for leaky surface acoustic wave generation. The IDT design minimizes propagation losses, bulk wave interferences, provides a highly linear phase response, and eliminates the need for impedance matching. As an example, a high frequency (~300-400 MHz) surface acoustic wave (SAW) transducer enables efficient excitation of shear-horizontal waves on 36° Y-cut lithium tantalate (LTO) giving a highly linear phase response (2.8° P-P). The sensor has the ability to detect at the pg/mm² level and can perform multi-analyte detection in real-time. The sensor can be used for rapid autonomous detection of pathogenic microorganisms and bioagents by field deployable platforms.

11 Claims, 10 Drawing Sheets

OTHER PUBLICATIONS

G.L. Harding et al, "Love wave acoustic immunosensor operating in liquid", Sensors and Actuators A 61 (1997) 279-286.

C.S. Hartmann et al, "Overview of Design Challenges for Single Phase Unidirectional SAW Filters", IEEE 1989 Ultrasonics Symposium, pp. 79-89.

Falk Herrmann et al, "Properties of Sensors Based on Shear-Holizontal Surface Acoustic Waves in $LiTaO_3/SiO_2$ and $Quarta/SiO_2$ Structures", IEEE Transactions on Ultrasonics, Ferroelectrics, and Frequency Control, vol. 48, No. 1, Jan. 2001, pp. 268-273.

T. Kodama et al, "Design of Low-Loss SAW Filters Employing Distributed Acoustic Reflection Transducers", IEEE 1986 Ultrasonics Symposium, pp. 59-64.

G. Kovacs et al, "Love waves for (bio)chemical sensing in liquids", IEEE 1992 Ultrasonics Symposium, pp. 281-285.

David A. Powell, et al, "A Layered SAW Device Based on $ZnO/LiTaO_3$ for Liquid Media Sensing Applications", 2002 IEEE Ultrasonics Symposium, pp. 493-496.

A. W. Warner et al, "Determination of Elastic and Piezoelectric Constants for Crystals in Class (3m)", The Journal of the Acoustical Society of America, vol. 42, No. 6, 1967, pp. 1223-1224.

Yongan Shui et al, "Optimization of Single-Phase, Unidirectional Transducers Using Three Fingers per Period", IEEE Transactions on Ultrasonics, Ferroelectrics, and Frequency Control, vol. 49, No. 12, Dec. 2002, pp. 1617-1621.

O. Tamarin et al, "Real time device for biosensing: design of a bacteriophage model using love acoustic waves", Biosensors and Bioelectronics, vol. 18, (2003) 755-763.

* cited by examiner

HIGH-FREQUENCY SHEAR-HORIZONTAL SURFACE ACOUSTIC WAVE SENSOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to biological sensing and, in particular, to a high-frequency interdigital transducer that is optimized to generate shear-horizontal surface acoustic waves on substrates supporting leaky waves for the detection biological analytes in a fluid.

BACKGROUND OF THE INVENTION

Microfabricated biological sensors based on acoustic devices combine a biologically active interface, which binds biological species (i.e., analytes) from an environment, with a physical transducer that provides an electrical output proportional to the amount of bound analyte. A commonly used acoustic device for biological sensing includes leaky surface acoustic wave (LSAW) sensors that rely on the electrical excitation of a shear-horizontal surface acoustic wave on a piezoelectric substrate. Typically, a wave is established on a surface and the collection of analyte mass on the surface influences the propagation of the surface wave. In particular, these analyte-induced changes can be sensed as variations in the velocity and amplitude of the surface wave.

Recently, Love wave sensors have received considerable attention for their high mass and viscous sensitivity with a minimal need for additional reagents. Minimizing the use of reagents is desirable for field deployable chem- and bio-detection systems. The transduction mechanism for Love wave sensors is based on propagating waves with a shear-horizontal (SH) polarization along the propagation direction. The SH polarization minimizes attenuation of the surface acoustic wave (SAW) into viscous media permitting detection in liquids. See G. Kovacs et al., *IEEE Ultrason. Symp.*, 281 (1992); G. Harding et al., *Sensors Actuators A* 61, 279 (1997); 0. Tamarin et al., *Biosensors and Bioelectronics* 18, 755 (2003); and D. W. Branch and S. M. Brozik, *Biosensors and Bioelectronics* 19, 849 (2003).

Love wave sensors comprise a piezoelectric substrate that primarily excites SH waves which are subsequently confined by a thin guiding layer. In general, if the layer material loads the substrate (i.e., the shear velocity in the layer is smaller than in the substrate), the SH bulk mode will become a surface mode having a single, transverse component of displacement confined within a few wavelengths of the surface. In particular, at high frequencies, such that the wavelength is less than the layer thickness, a surface Love wave can be concentrated in the thin waveguide layer. Therefore, the waveguide layer is crucial to achieve high sensitivity by having a low shear velocity compared to the substrate. See G. Kovacs et al., *IEEE Ultrason. Symp.*, 281 (1992); and Z. Wang and J. D. N. Cheeke, *Appl. Phys. Lett.* 64, 2940 (1994). For biodetection, the waveguide layer can also provide a mechanism for stable chemical attachment through covalent linkage of antibodies, DNA, or other biomolecules to achieve the required selectivity. Waveguide materials such as polymers, silicon dioxide ($SiO_2$), and more recently zinc oxide (ZnO) are in use. See E. Gizeli et al., *IEEE Trans. Ultrason. Ferroelect. Freq. Contr.* 39, 657 (1992); F. Herrmann et al., *IEEE Trans. Ultrason. Ferroelect. Freq. Contr.* 48, 268 (2001); and D. A. Powell et al., *IEEE Ultrason. Symp.*, 493 (2002).

However, piezoelectric substrates that support such leaky surface acoustic waves, such as Love waves, require advanced transducer designs to avoid excitation of undesired modes. Unlike Rayleigh wave devices, where a true surface wave exists in the absence of dispersion, LSAW transducers require that bulk waves are suppressed and that intra-device acoustic reflections are minimized. Existing bidirectional transducers have major drawbacks in this regard since waves are launched in both the forward and backward directions and are complicated by bulk wave generation. Above about 100 MHz, the phase is highly non-linear and other modes interfere with the main SH sensing mode. Although edge reflections from backward traveling waves can be easily suppressed on substrates that support Rayleigh waves through the use of absorbers, this it not possible on substrates that support leaky waves. Moreover, since surface-skimming bulk waves (SSBW) propagate with a velocity very close to the leaky or shear horizontal mode on piezoelectric substrates, such as 36° YX lithium tantalate (LTO), the design of the transducer is highly critical to exciting the proper mode, especially at high frequencies. The design is further complicated by the fact that the electrode metal thickness determines the degree of propagation loss for leaky waves on LTO.

Therefore, a need exists for a SH surface acoustic wave (Love wave) sensor comprising a high-frequency interdigital transducer that provides low insertion loss and high out-of-band rejection, while suppressing bulk wave excitation at the stop band, to enable high sensitivity detection of biological and chemical analytes in a fluid.

SUMMARY OF THE INVENTION

The present invention is directed to a shear-horizontal surface acoustic wave sensor comprising a piezoelectric substrate, a unidirectional transmitting interdigital transducer on the substrate that primarily excites a shear-horizontal wave in the substrate, a guiding layer on the substrate that has a lower shear velocity than the substrate for confinement confines the shear-horizontal wave therein as a guided Love wave, a sensing region on the guiding layer, and a unidirectional receiving interdigital transducer that detects the guided Love wave that is transmitted through the sensing region.

The interdigital transducers can comprise a single-phase unidirectional transducer, such as an electrode-width-controlled single-phase unidirectional transducer. The transmitting and receiving interdigital transducers can be in a delay-line configuration. The frequency of the guided Love wave can be greater than 100 MHz. Piezoelectric substrates that excite either pure or leaky shear-horizontal mode generation include 36° Y quartz, 36° YX lithium tantalate, langasite, langatate, langanite, lead zirconate titanate, cadmium sulfide, berlinite, lithium iodate, lithium tetraborate, and bismuth germanium oxide. Alternatively, the sensor can comprise a piezoelectric crystal layer on a rigid non-piezoelectric substrate. The guiding layer can comprise a polymer, $SiO_2$, or ZnO. The guiding layer is rendered biologically active by conjugating a layer of receptors such as antibodies, proteins, aptamers, or ligands that bind analytes from a fluid. Similarly, the sensor can detect chemicals in fluids through binding to a chemically sensitive interface.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
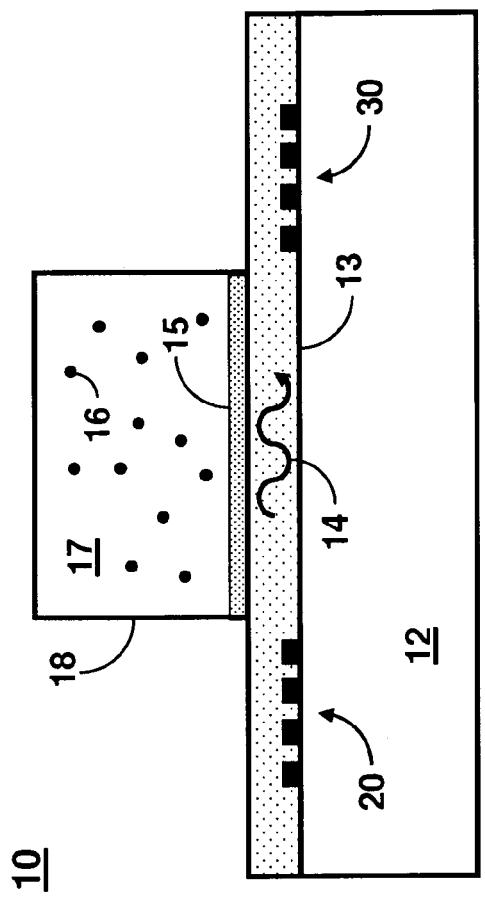
FIG. 1 shows a schematic side-view illustration of a Love wave sensor.

In FIG. 1 is shown a schematic side-view illustration of a shear-horizontal SAW (Love wave) sensor 10 of the present invention. The Love wave sensor 10 comprises a piezoelectric substrate 12, a transmitting interdigital transducer (IDT) 20 that primarily excites SH waves in the piezoelectric substrate 12, a thin guiding layer 13 that confines the SH wave as a Love wave 14, and a receiving IDT 30 that detects the guided Love wave 14 in a delay-line configuration. To obtain low device loss, the delay line is preferably reciprocal with a receiving IDT 30 that is equivalent to the transmitting IDT 20. The sensor 10 can further comprise electrical tuning circuits (not shown) for optimizing IDT electrical connections with external electrical components, such as a voltage source or electrical load. The thin guiding layer 13 is built on the piezoelectric substrate 12. The guiding layer 13 comprises a material that has shear velocity that is smaller than the substrate 12 to confine the Love wave. The waveguide layer 13 can also provide a mechanism for attachment of a biological or chemical analyte 16 from a liquid medium 17. For example, the waveguide layer 13 can further comprise a chemically or biologically sensitive layer or interface 15 that sorbs or captures the analyte 16 from the liquid. The layer or interface 15 can comprise a material that is sensitive and selective to the specific analyte to be detected. A fluid cell 18 can provide for delivery of the analytes 16 to the interface 15.

The delay line can be configured such that acoustic waves are launched and received after traveling through the liquid-interface sensing region 15 of the guiding layer 13. When a radio frequency (RF) voltage is applied to the electrical port of the transmitting IDT 20, a SH wave is generated in the substrate 12 and subsequently confined as a Love wave 14 in the guiding layer 13. The receiving IDT 30 can detect the Love wave 14 by transducing the mechanical wave back into an electrical signal by inverse piezoelectric coupling. Added mass from the captured analyte perturbs the propagation velocity of the Love wave in the guiding layer. In the delay-line configuration, the open loop operation at constant frequency provides relative phase shifts for each delay-line channel.

Figure 10:
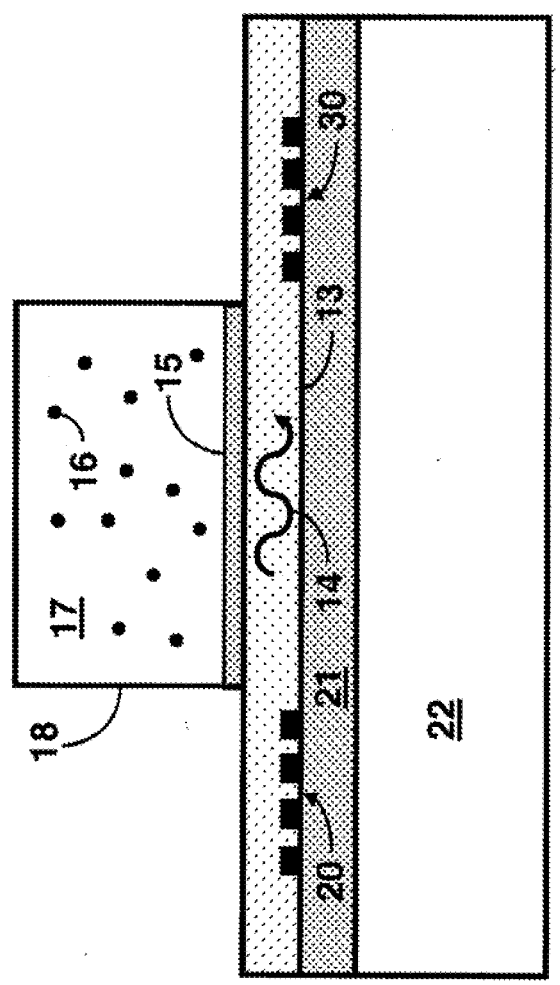
FIG. 10 shows a schematic side-view illustration of a Love wave sensor, comprising a thin piezoelectric crystal layer on a rigid, non-piezoelectric substrate.

The substrate preferably comprises a piezoelectric crystal that has a high electromagnetic coupling coefficient and can propagate a LSAW with high velocity. The substrate can be a precisely oriented piezoelectric crystal plate that can generate a SAW having SH polarization along the propagation direction. For example, the crystal plate can comprise 36° Y quartz, 36° YX LTO, langanite, langatate, langanite, lead zirconate titanate (PZT), cadmium sulfide (CdS), berlinite, lithium iodate ($LiIO_3$), lithium tetraborate ($Li_2B_4O_7$), or bismuth germanium oxide ($Bi_{12}GeO_{20}$) which support either leaky or true SH waves. See M. P. Cunha et al., *Ultrason. Symp.*, 381 (2002); and E. Berkenpas et al., *Ultrason. Symp.*, 1404 (2003). The electromagnetic coupling coefficient ($K^2$) is a measure of the efficiency of the piezoelectric material in converting an applied electrical signal into mechanical energy of the SAW. Preferably, the substrate comprises a strong piezoelectric material, such as 36° Y-cut LTO which exhibits strong coupling ($K^2$=6.6%) for propagation of a leaky SH-type wave along the X-axis. The strong coupling on LTO provides advantages over substrates such as 36° Y quartz where exquisite care in the fluidic packaging is required to prevent excessive wave damping and hence high insertion losses. Alternatively, as shown in FIG. 10, the substrate can comprise a thin piezoelectric crystal layer 21 that is thicker than the SAW penetration depth (i.e., greater than a few acoustic wavelength thickness) on a rigid, non-piezoelectric substrate 22. For example, the thin crystal layer can comprise a piezoelectric film of ZnO or AlN on the substrate. These materials can be deposited by sputtering or sol-gel methods.

The guiding layer comprises a waveguide material that has shear velocity that is smaller than the substrate to support the existence of Love waves. Preferably, the waveguide material has low acoustic loss, low acoustic propagation velocity, chemical stability in fluid environments, capability of being deposited on piezoelectric substrates, and is suitable for chemical attachment of biological receptors. For example, the waveguide material can be a polymer, $SiO_2$, or ZnO.

An IDT comprises opposing comb-shaped electrodes, each having a fingerlike periodic pattern of electrode fingers interdigitated with the electrode fingers of the opposing comb-shaped electrode. The electrodes can be formed of any suitable conductive material. An acoustic cell within the IDT is defined in terms of the periodicity of the finger structure that is specified in terms of the acoustic wavelength. This cell pattern often repeats for a specific number of wavelengths which defines the overall acoustic length of the IDT. When a RF drive voltage is applied to the comb-shaped electrodes of the transmitting IDT, a spatially periodic, surface-concentrated electric field distribution is established between the spatially periodic electrode fingers that penetrates into the piezoelectric substrate. Because of the piezoelectric coupling, an elastic strain distribution with periodicity is created in the substrate, thereby generating the acoustic wave. To generate the correct acoustic wave, the proper axis of the piezoelectric crystal is preferably aligned with the IDT. The strength of the outputted acoustic wave can be controlled by changing the overlap of the electrodes, number of finger pairs, their periodicity, the finger pattern, and the power input.

The bandwidth of the delay line is determined by the design of the transmitting and receiving IDTs, coupling constant of the piezoelectric substrate, and insertion loss. Insertion losses arise from bidirectional and reflection losses of the IDTs, excitation of undesired modes, material losses, diffraction effects, beam steering effects due to misorientation of the transducers, and any electrical mismatches. Spurious signals arising from these effects can cause a nonlinear response that can severely restrict the dynamic range of the delay line. Existing bidirectional LSAW transducer designs produce highly non-linear phase responses, causing the monitored phase response to shift in a non-linear fashion.

The SH-SAW sensor of the present invention comprises a unidirectional interdigital transducer, wherein acoustic waves are generated predominantly in one direction. The unidirectional IDT uses the bidirectional aspect of a single excitation electrode finger and grounded metal reflectors. The unidirectional IDT structure comprises electrodes that cause the phases from each of the spatially separated excitation electrode fingers to be in-phase. Unidirectionality can be achieved by introducing reflectors or passive electrode fingers between parts of the transducer. The placement of the reflectors is such that they selectively enhance the generated signal in the forward direction while the reflections reduce the size of the signal transduced in the reverse direction. The spacing between the bidirectional excitation electrodes and the reflectors is optimized to create acoustic waves that are in-phase along the length of the transducer. The finger spacing can be on-order of the finger width. The metal thickness of the fingers also impacts the reflectivity of the overall structure and can be optimized to reduce mode conversion (i.e., energy loss to the substrate). Therefore, a unidirectional transducer with appropriate phasing can achieve a high level of directivity and provide frequency scalability for a variety of sensor applications.

The unidirectional IDT preferably comprises a single-phase unidirectional transducer (SPUDT). A SPUDT deliberately includes reflections internal to the transducer to cancel the effects of regeneration reflection. The SPUDT can be a double-metallization SPUDT structure, a natural SPUDT (NSPUDT), or an electode-width-controlled SPUDT (EWC-SPUDT). See Wright, U.S. Pat. No. 5,073,763; Bergmann et al., U.S. Pat. No. 6,777,855; and Hartmann et al., U.S. Pat. No. 7,173,360; which are incorporated herein by reference. SPUDTs can comprise interdigitated electrode fingers that are clustered in periodically spaced ladder-type finger groups, or "cells." The unidirectional IDT can further comprise SAW reflection gratings interspersed within the finger cells.

For example, a EWC-SPUDT can be used to optimize excitation of SH waves on 36° Y-cut LTO at frequencies in excess of a few hundred MHz. The major design goal of the SPUDT is to achieve high directivity in the forward acoustic port while maintaining good impedance matching on the electrical port. Unidirectionality of the SPUDT is achieved when the distance of the reflection center (RC) is set as $(2n+1)\lambda/8$ (where n=1, 2, 3 . . . m, and $\lambda$ is the acoustic wavelength) from the transduction center (TC). See C. S. Hartmann et al., *IEEE Ultrason. Symp.*, 79 (1989); T. Kodama et al., *IEEE Ultrason. Symp.*, 59 (1986); and B. J. Hunsinger et al., U.S. Pat. No. 4,162,465; which are incorporated herein by reference. With an excitation electrode width of $\lambda/8$, the phase shift between the reflector and transduction centers is $+/-\pi/2$. The resulting SPUDT can have low insertion loss and good triple transit suppression at the center frequency simultaneously. Thus, the IDT of the present invention can concentrate the energy of the SH-SAW in one direction for leaky SAW substrates, such as 36° YX LTO, and is also suitable for substrates supporting true SH waves, such as langasite, langatate, or langanite. Such an IDT is advantageous for SH-SAW sensor applications where the leaky type propagation is far more stringent than Rayleigh-based SAW designs.

The operational frequency of the transducer is given by $f=v_s/8d$, where d is the width of the excitation finger and $v_s$ is the velocity of the SH wave. The upper limit in frequency is dictated by lithographic patterning limit for the smallest structure in the SPUDT design. For example, a smallest feature size of $\lambda/8$ gives an upper limit of about 1.7-2.0 GHz on 36° YX LTO using a photolithographic pattern resolution of 0.3 µm. However, for fluid sensing applications, operating at the IDT at 2 GHz reduces the wave penetration depth to only 12 nm in the fluid. This decay length is still suitable for protein detection applications, but may be unsuitable for the detection of larger antigens, such as spores and bacteria.

Figure 2:
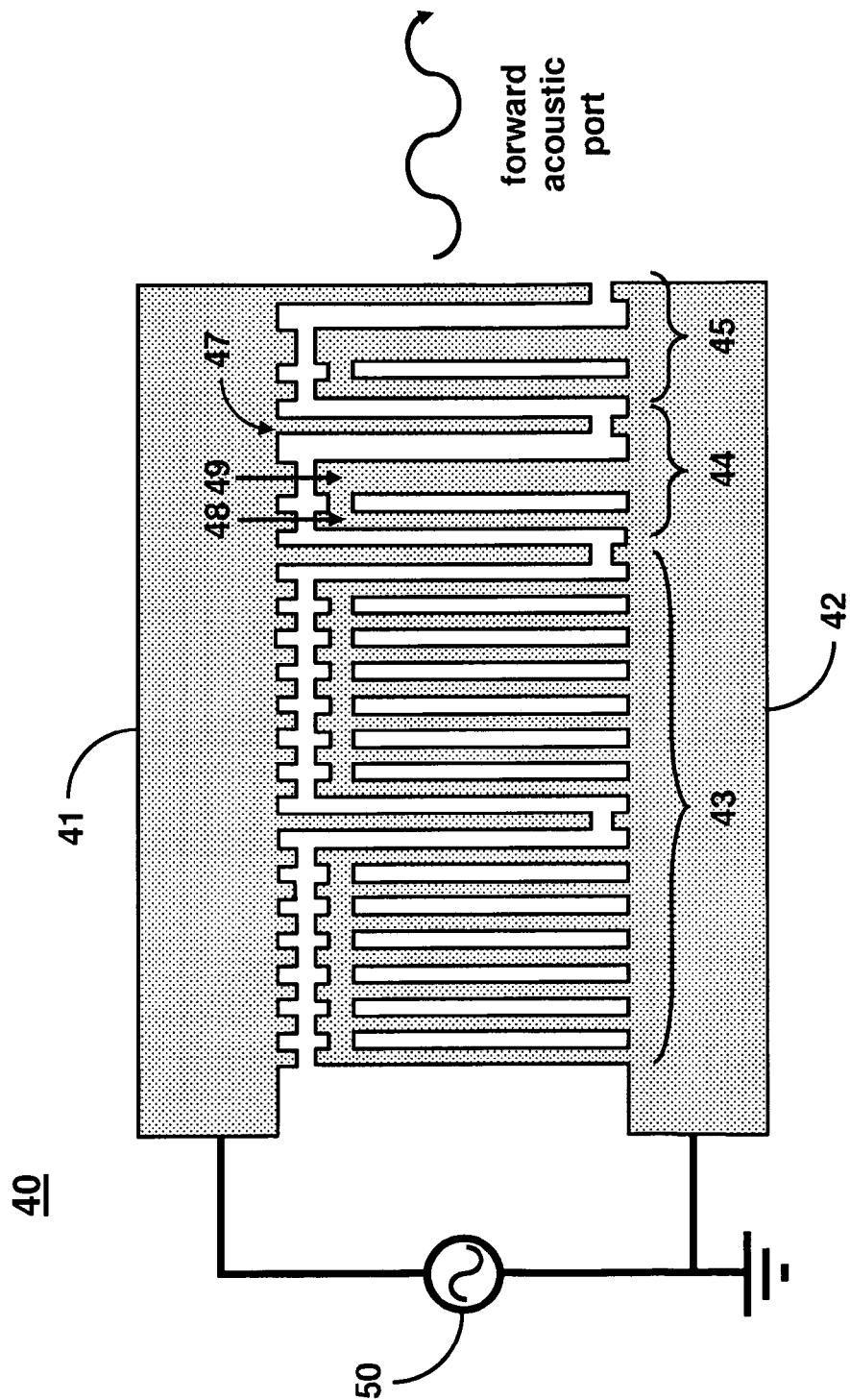
FIG. 2 shows a schematic top-view illustration of a SPUDT for a Love wave sensor.

FIG. 2 shows a schematic top-view illustration of an exemplary unidirectional IDT 40 comprising EWC-SPUDT cells and a reflection grating to achieve low insertion loss and high out-of-band rejection, while minimizing bulk wave excitation at the stop band. This exemplary transducer comprises opposing comb-shaped electrodes 41 and 42, each having current-collecting bus bar and a fingerlike periodic pattern of electrode fingers interdigitated with the electrode fingers of the opposing comb-shaped electrode. A RF voltage from an electrical source 50 is applied to the electrical port of the opposing comb-shaped electrodes of the transmitting IDT 40 (a receiving IDT would have an electrical load coupled across the comb-shaped electrodes to transduce the mechanical acoustic wave back into an electrical signal by inverse piezoelectric coupling). This IDT comprises a reflection grating 43 and two SPUDT cells 44 and 45. The length of a SPUDT cell is approximately $\lambda$, where $\lambda$ is the center frequency of the transducer. Each SPUDT cell comprises a distributed reflector comprising a single $\lambda/8$ excitation electrode finger 47 and $\lambda/8$ and $\lambda/4$ reflection electrodes 48 and 49. Additional n SPUDT cells can be used to produce a smaller passband. Optimization procedures have been developed to tune SPUDT designs for non-leaky piezoelectric substrates, such as 128° YX lithium niobate. See Y. Shui et al., *IEEE Trans. Ultrason. Ferroelectr. Freq. Cntrl.* 49, 1617 (2002), which is incorporated herein by reference. The SPUDT structure can be further analyzed using theoretical and experimental methods to tune the electrode spacings for optimal response on SH piezoelectric substrates.

Figure 3:
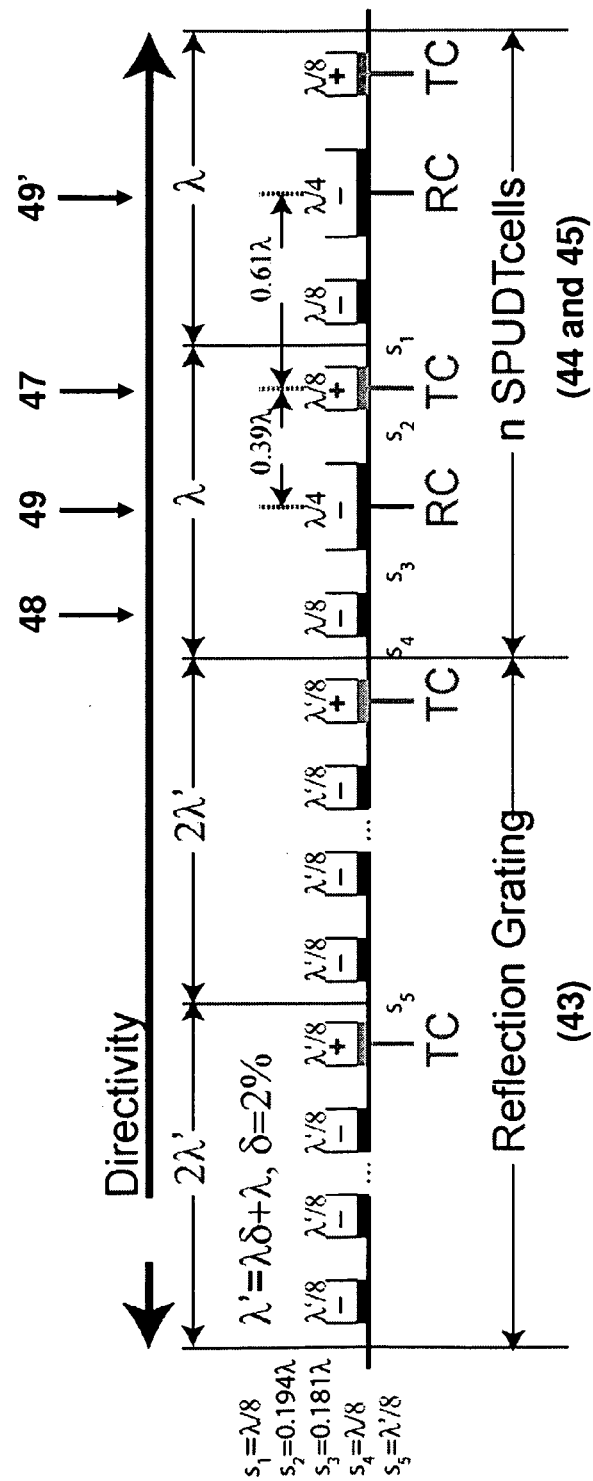
FIG. 3 shows a schematic side-view illustration of a SPUDT that uses distributed reflectors consisting of both $\lambda/8$ and $\lambda/4$ fingers to enhance reflection of the bidirectional acoustic waves.

FIG. 3 shows a schematic side-view illustration of the exemplary unidirectional IDT that uses distributed reflectors consisting of both $\lambda/8$ and $\lambda/4$ fingers to enhance reflection of the bidirectional acoustic waves. The reflector uses a slightly shifted cell dimension since the waves are dispersive. The spacing between the TC excitation electrode 47 and RC reflection electrode 49 in a SPUDT cell is 0.39, and the spacing to the forward RC 49' is 0.61λ which was optimized experimentally for use with leaky SAW substrates. The reflection grating 43 consists of two cells made from $\lambda'/8$ electrodes, where $\lambda'=\lambda\delta+\lambda$, where $\delta=2\%$. Since the waves are dispersive in nature the width adjustment of the reflectors in the grating enhances the reflectivity of the structure, improving the unidirectionality beyond a conventional EWC-SPUDT design on 36° YX LTO. This SPUDT design enables the use of SH-SAW based sensors at much higher frequencies due to the reduction of inter-IDT acoustic reflections while maintaining a high level of directivity. In this way, the bulk modes that are present in conventional bidirectional IDTs are not excited.

Waveguide Thickness and Sensor Sensitivity

The dispersion behavior of an exemplary SPUDT on an LTO substrate loaded with a waveguide layer and an additional mass layer was computed by extending the Green's function method to include an isotropic film and mass layer. See D. Qiao et al., *IEEE Trans. Ultrason. Ferroelectr. Freq. Cntrl.* 46, 1242 (1999). From $kG_{44}(s)$, the effective permittivity was computed to find the propagating velocities as the waveguide layer thickness increased. For comparison, the multilayered problem was analyzed using an isotropic model. In the isotropic case, the substrate phase velocity was taken as $V_s$=4040 m/s since the surface of the LTO is loaded by a 5000 Å aluminum layer. The shear velocity in the waveguide was $V_w$=2852 m/s and mass layer was $V_m$=1300 m/s. The density for each layer was $\rho_s$=7450 kg/m³, $\rho_w$=2200 kg/m³, and $\rho_m$=1200 kg/m³.

Figure 4:
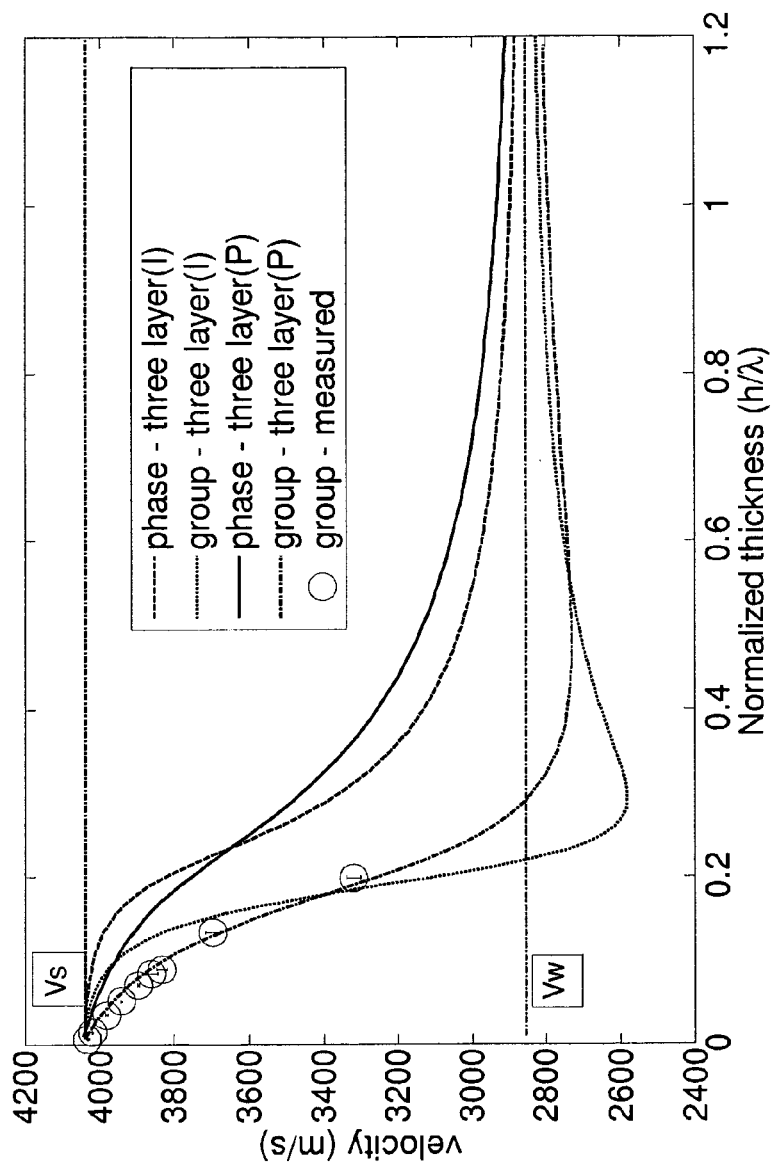
FIG. 4 shows dispersion curves for $SiO_2$ on 36° YX LTO. (I): isotropic model, (P) piezoelectric model. The group velocity was measured using time domain analysis. $V_s$ and $V_w$ lines denote the shear velocity in the substrate and waveguide, respectively.

The piezoelectric constants for LTO were taken from A. W. Warner et al., *J. Acoust. Soc. Amer.* 42, 1223 (1967). As shown in FIG. 4, the dispersion behavior indicates a significant difference between the isotropic and piezoelectric model due to stiffening. Excellent agreement was observed between the measured and computed group velocities for the $SiO_2$ waveguide confirming the piezoelectric model.

Figure 5:
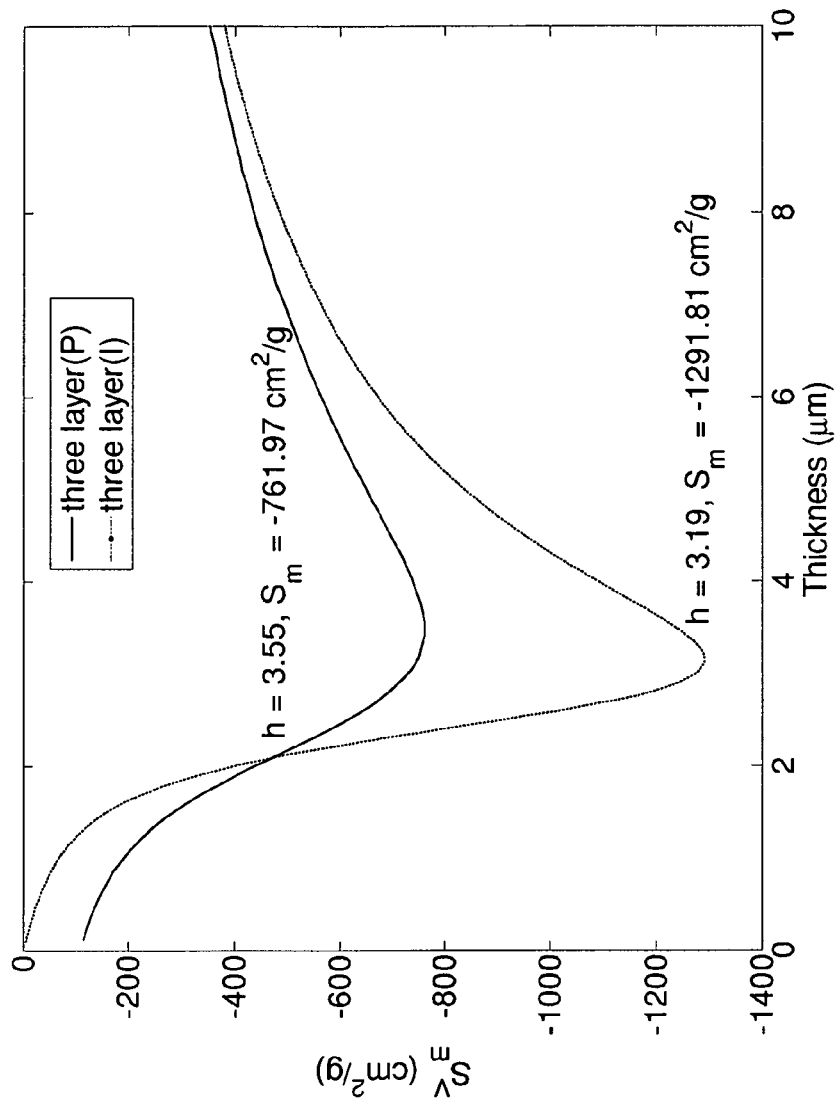
FIG. 5 shows sensitivity curves for $SiO_2$ waveguide on 36° YX LTO. (I): isotropic model, (P) piezoelectric model. $\lambda$=12.4 μm.

To determine the sensitivity, the dispersion curves were computed with and without an additional mass layer. The mass sensitivity due to the velocity shift was computed using $$S_m^V = \frac{1}{V_o} \frac{\partial V}{\partial m} \quad (1)$$

where V is the phase velocity, $V_0$ is the phase velocity in the absence of the mass layer with mass $m=\rho_m \epsilon_m$ and $\epsilon_m$ is the thickness of the mass layer. The calculation includes the properties of the mass layer ($V_m$=1200 m/s, $\rho_m$=1300 kg/m³). As shown in FIG. 5, the relative error of the optimal thickness (h) was 10%, whereas the relative error of the maximum sensitivity ($S_m$) was nearly 70%. This theoretical sensitivity analysis indicates that isotropic models are insufficient to predict sensitivity for 36° YX LTO, despite that the model predicts the optimal waveguide thickness within 10% of the piezoelectric model. This suggests that to determine the mass sensitivity for strongly coupled substrates, such as LTO, piezoelectric models are required. Since higher operating frequencies require thinner oxide layers the instability and uniformity issues common with thicker oxide layers are reduced.

Example

Love Wave Sensor Fabrication

As an example of the present invention, a SPUDT was fabricated that enabled high frequency (330 MHz) excitation of the SH-type wave on LTO for array operation. The wavelength is of order 10 μm for most materials at an operating frequency of 330 MHz, therefore these transducers can be fabricated using standard photolithographic techniques. Love wave sensors were fabricated using 36° YX LTO wafers that were 510 μm thick by 100 mm in diameter, and single-side polished. Prior to metallization of the IDTs, wafers were cleaned in a barrel asher, followed by dipping in 1 vol % hydrofluoric acid (HF). A negative-tone photoresist (PR) was applied onto the wafer using a spin coater with a Gyrset lid to achieve a thickness of 2.0 μm. After patterning, the wafers were metallized with 50 Å of titanium for improved adhesion followed by 5000 Å aluminum using an electron-beam evaporator. An acetone bath was used to perform the lift-off, followed by rinsing in methanol, isopropyl alcohol, and de-ionized water. This was repeated for the metallization of the ground plane, buss lines, and contact pads with the appropriate photomask.

Silicon dioxide waveguides up to 2.0 μm in thickness were deposited onto the entire wafer using plasma-enhanced chemical vapor deposition (PECVD). A positive-tone PR was spin coated at 2000 rpm and 3000 rpm/sec. A photoresist mask was used to "open" the $SiO_2$ over the electrical contact pads. The $SiO_2$ was etched by reactive ion etching (RIE). Each Love wave sensor had four delay lines per die. Each die was 10×12 mm², yielding 44 Love wave sensor arrays per wafer.

Biological Materials and Sensor Preparation

Three IgG antibody types (anti-avidin IgG antibody, anti-BSA, and (goat) anti-mouse IgG) were used to perform multi-analyte detection using the Love wave sensor array. Each antibody was biotinylated using sulfo-LC-biotin. Excess biotinylating agent was removed by centrifugation using YM-50 Millipore Microcon® filters.

The sensors were cleaned in acetone, methanol, and isopropanol, rinsed in distilled water, followed by exposure to UV-ozone for 15 minutes in a UV-Ozone cleaner. An amine reactive surface was prepared on the $SiO_2$ waveguides using 1% (3-glycidoxypropyl)trimethoxysilane (3-GPS) in toluene. NeutrAvidin was applied to the 3-GPS layer at 0.25 mg/ml for 30 minutes. Each biotinylated antibody was reacted with the NeutrAvidin for 30 minutes using an adsorption cell to confine the antibody types over each channel. This procedure produced covalently attached IgG antibodies to the $SiO_2$ waveguide.

Measurements and Data Acquisition

The sensors were measured using a network analyzer. The data acquisition system measured all four delay-line channels simultaneously. Phase data was recorded in real time using a 14-bit A/D converter at a rate of 1000 samples/second. The data was acquired using both a laptop computer and Personal Digital Assistant (PDA). Fluid injections were performed using a syringe pump connected to a six-port two position flow valve. The flow rate was 10 μl/min and fluid cell volume was 4 μl.

Mass Sensitivity

The mass sensitivity was determined for the Love wave sensors using calibrated fluids with known density and viscosity. See A. Malavé et al., *IEEE Sensors*, 604 (2006). Four fluid samples were prepared with known amounts of glycerin and applied to the sensors. Subsequently, the phase shift was measured after each injection and repeated four times. The resulting slope ($\Delta\phi/\sqrt{\rho\eta}$) was determined by a linear fit procedure and used to calculate mass sensitivity and detection limit for a given noise level and phase resolution.

Exemplary Love Wave Sensor Response

IDT Response

Figure 6A:
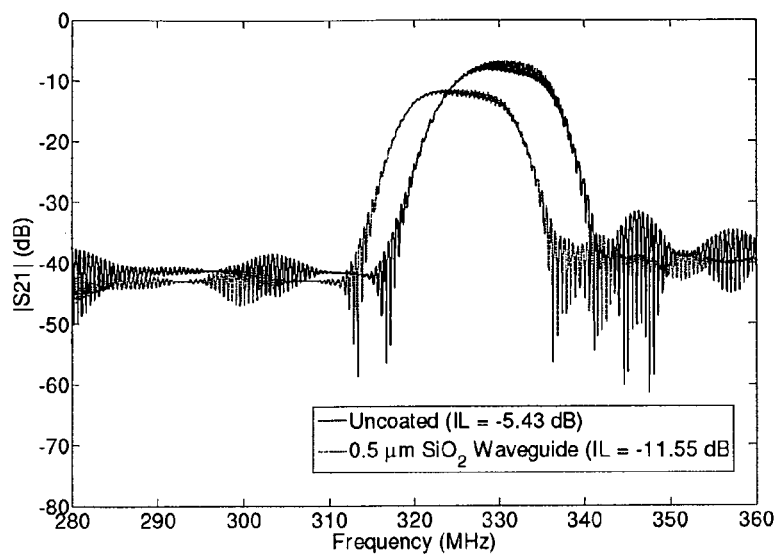
FIG. 6 shows measured S21 response of a 330 MHz Love wave sensor a) |S21| (dB) and b) phase)(°). Increasing the waveguide thickness increased the phase slope.
Figure 6B:
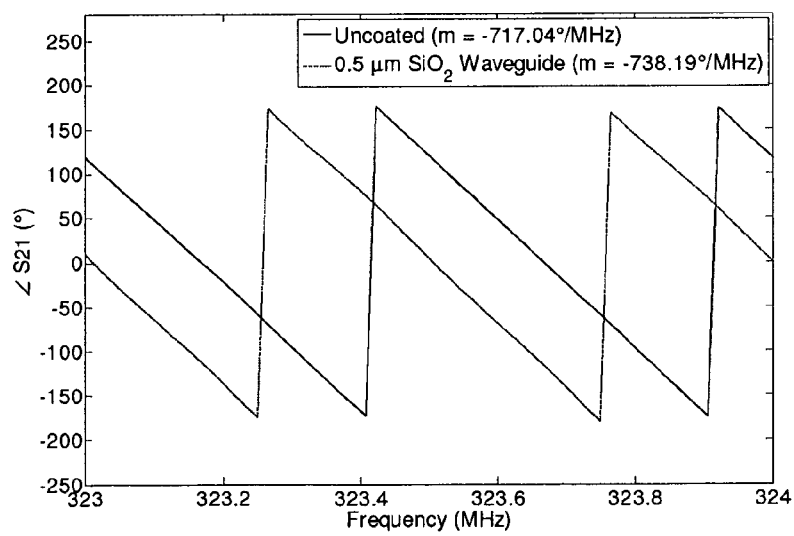

As shown in FIG. 6, this IDT had a highly linear phase response (2.8° P-P) with an insertion loss of −5.43 dB at 330 MHz. The phase linearity was maintained after the deposition of a 0.5 μm $SiO_2$ waveguide. The IDT design proved successful toward suppressing bulk waves and preferentially exciting the leaky SH mode on 36° YX LTO. The low degree of phase ripple was ideal toward achieving a linear sensor calibration. When used in an array, the cross-talk was only −39 dB and can be completely eliminated in multiplexed operation. Increasing the operation frequency further for Love wave sensors would limit the ability to detect larger antigens. The wave penetration into the fluid decreases as $1/\sqrt{v}$, where $v$ is the operating frequency. At 330 MHz, the penetration depth is 31 nm in water.

Waveguide Variability

Figure 7:
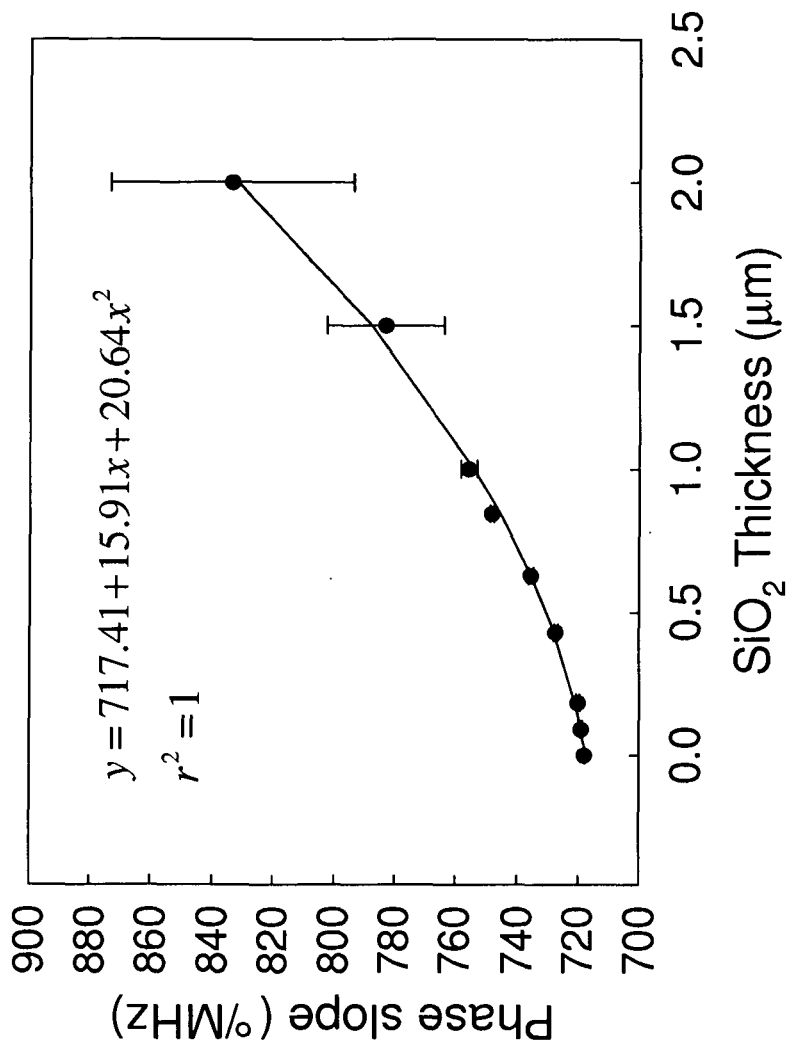
FIG. 7 shows phase slope variability as the waveguide thickness increased. The slope of S21(ν) (°/MHz) is an indicator of sensitivity.

As shown in FIG. 7, significant phase slope variation (°/MHz) was observed as the waveguide thickness was increased. This indicated that even for a highly uniform oxide deposition process (1-2% in thickness) across the wafer, the sensitivity is expected to vary significantly die to die when the waveguide is greater than 2 μm. This problem is slightly mitigated for Love wave sensors operating above 300 MHz, where the waveguide is only a few microns. At the wafer level, a uniform waveguide is desirable to achieve sensor reproducibility.

Mass Sensitivity and Multi-Analyte Biodetection

Figure 8:
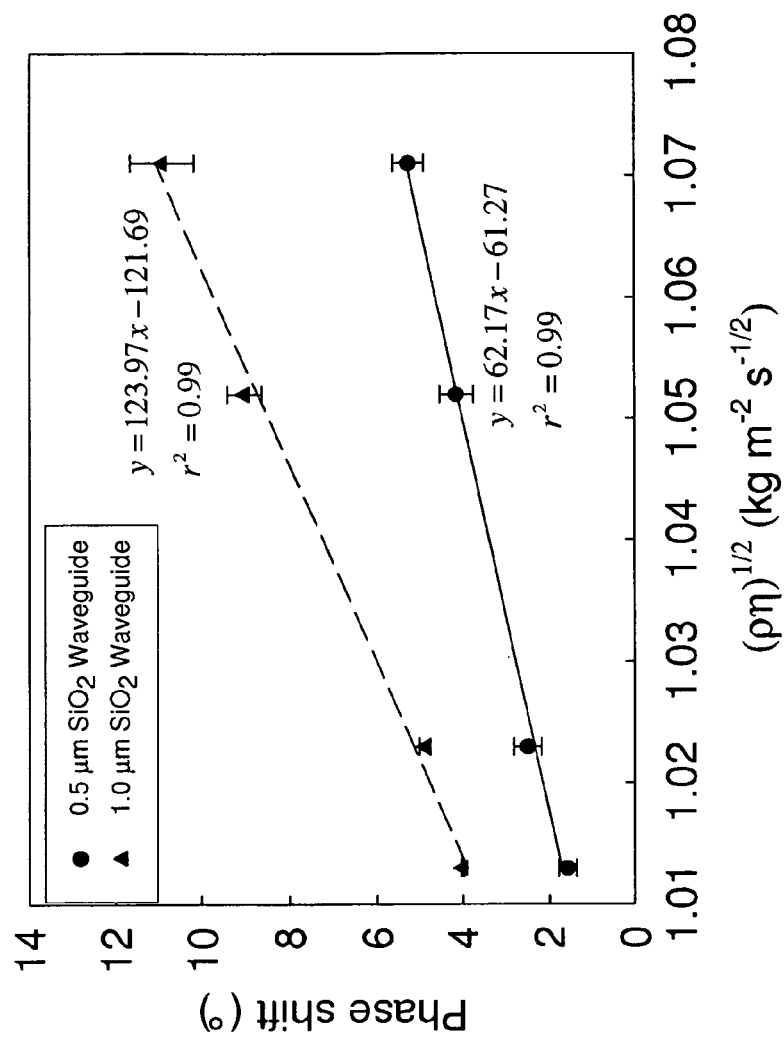
FIG. 8 shows phase shift due from glycerin solutions with varying density (ρ) and viscosity (η). —line: 0.5 μm waveguide and —line: 1.0 μm waveguide.

FIG. 8 shows the mass sensitivity that was measured using the Love wave sensors at waveguide thicknesses of 0.5 μm and 1.0 μm. The results indicate sensitivities of 4.31±0.33° mm$^2$/ng for the 0.5 μm and 7.19±0.74° mm$^2$/ng for the 1-μm waveguides. This translates to a detection limit of 6.7±0.40 pg/mm$^2$ at 0.01° phase resolution assuming five times the noise level as a conservative value.

Using three different antibodies covalently attached to the Love wave sensor array, the presence of avidin, BSA, and mouse antigens were detected in real time. The injected concentration for each antigen was 100 ng/ml (5 μl volume). The carrier buffer was 1×PBS pH 7.2. The buffer for each antibody solution was identical to the carrier buffer to minimize viscosity shifts during injection. The fluid cell dwell time was 24 seconds.

Figure 9:
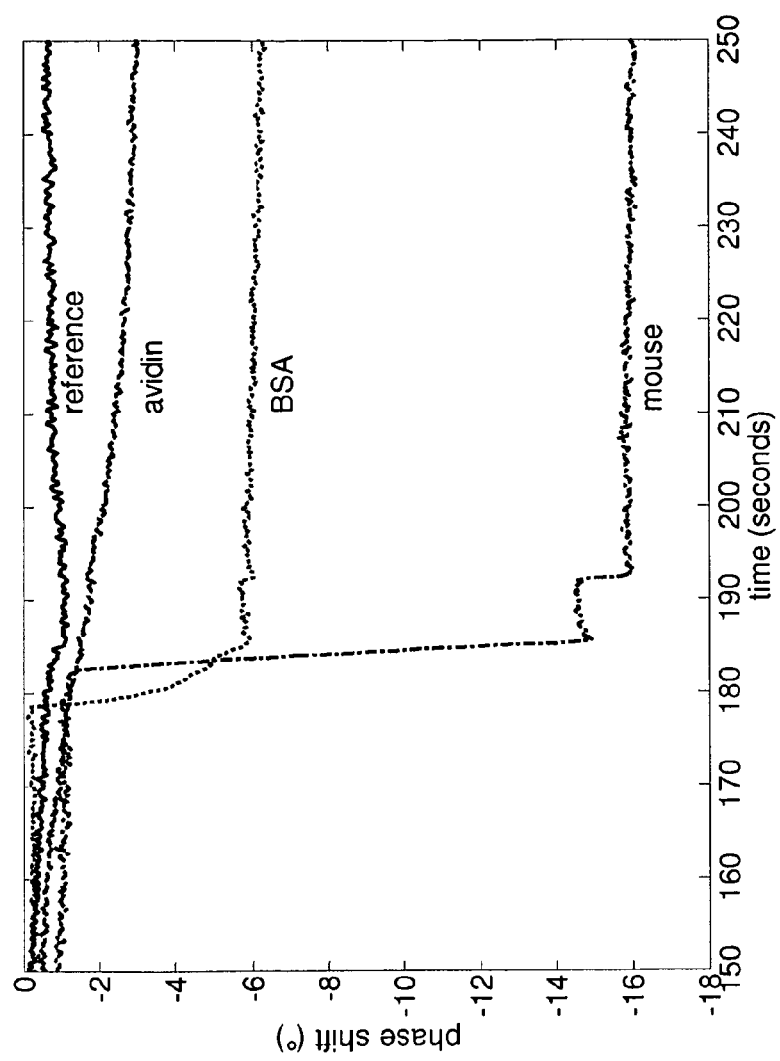
FIG. 9 shows multi-analyte biodetection of three antigens in real-time.

In FIG. 9 is shown the phase response for each Love wave sensor. Since the fluid cell was 4 μl, the mean protein diffusion time was about ten seconds, thus the phase response was very rapid. The difference in phase responses was due to variation in binding affinities amongst the antibodies. A separate analysis is required to determine the antibody avidity to each of their intended antigens then compare with the array results.

The present invention has been described as a high-frequency shear-horizontal surface acoustic wave (Love wave) sensor. It will be understood that the above description is merely illustrative of the applications of the principles of the present invention, the scope of which is to be determined by the claims viewed in light of the specification. Other variants and modifications of the invention will be apparent to those of skill in the art.

I claim:

1. A shear-horizontal surface acoustic wave sensor, comprising:
   a piezoelectric substrate,
   a unidirectional transmitting interdigital transduce on the substrate that primarily excites shear-horizontal waves on the substrate,
   a guiding layer on the substrate that has a lower shear velocity than the substrate for confinement of the shear-horizontal wave therein as a guided Love wave,
   a sensing region on the guiding layer, and
   a unidirectional receiving interdigital transducer that detects the guided Love wave that is transmitted through the sensing region,
   wherein the unidirectional transmitting and receiving transducers each comprise an electrode-width-controlled single-phase unidirectional transducer (EWC-SPUDT) comprising at least one EWC-SPUDT cell, each EWC-SPUDT cell comprising a λ/8 excitation electrode finger and λ/8 and λ/4 reflection electrode fingers, and wherein the finger spacings are optimized to excite or detect shear-horizontal waves that are in-phase along the length of each transducer in the presence of the guiding layer and the sensing region.

2. The sensor of claim 1, wherein the unidirectional transmitting and receiving interdigital transducers are configured in a delay-line configuration.

3. The sensor of claim 1, wherein the frequency of the guided Love wave is greater than 100 MHz.

4. The sensor of claim 3, wherein the frequency of the guided Love wave is greater than 300 MHz.

5. The sensor of claim 1, wherein the piezoelectric substrate 36° YX lithium tantalate.

6. The sensor of claim 1, wherein the piezoelectric substrate comprises 36° Y quartz, langasite, langatate, langanite, lead zirconate titanate, cadmium sulfide, berlinite, lithium iodate, lithium tetraborate, or bismuth germanium oxide.

7. The sensor of claim 1, wherein the substrate comprises a piezoelectric crystal layer, that is approximately thicker than the Love wave penetration depth, on a non-piezoelectric substrate.

8. The sensor of claim 1, wherein the guiding layer comprises a polymer, SiO$_2$, or ZnO.

9. The sensor of claim 1, wherein the guiding layer comprises a biologically sensitive interface for capturing analytes from a fluid on the guiding layer in the sensing region.

10. The sensor of claim 1, wherein the guiding layer comprises a chemically sensitive interface for sorbing analytes from a fluid on the guiding layer in the sensing region.

11. The sensor of claim 1, further comprising a detector for measuring the phase response of the guided Love wave as a function of analyte added to the guiding layer in the sensing region.

* * * * *

UNITED STATES PATENT AND TRADEMARK OFFICE
CERTIFICATE OF CORRECTION

PATENT NO.        : 8,436,509 B1
APPLICATION NO.   : 12/169239
DATED             : May 7, 2013
INVENTOR(S)       : Darren W. Branch It is certified that error appears in the above-identified patent and that said Letters Patent is hereby corrected as shown below:

On the title page, in column 1, item "(73) Assignee", line 1, please delete the word "Saudia" and insert the word --Sandia--.

Signed and Sealed this
Fifth Day of April, 2016

Michelle K. Lee
*Director of the United States Patent and Trademark Office*